United States Patent [19]
Silvian

[11] Patent Number: 4,847,617
[45] Date of Patent: Jul. 11, 1989

[54] HIGH SPEED DIGITAL TELEMETRY SYSTEM FOR IMPLANTABLE DEVICES

[75] Inventor: Sergiu Silvian, Pasadena, Calif.

[73] Assignee: Siemens-Pacesetter, Inc., Sylmar, Calif.

[21] Appl. No.: 85,914

[22] Filed: Aug. 14, 1987

[51] Int. Cl.⁴ ..................... G08B 21/00; G08C 19/28
[52] U.S. Cl. ..................... 340/870.160; 340/870.390; 340/310 R; 128/419 R; 128/420 R; 600/12
[58] Field of Search ..................... 340/870.39, 870.16, 340/310 R; 128/1.4, 1.5, 696, 419 R, 419 PS, 419 PT, 420 R

[56] References Cited

U.S. PATENT DOCUMENTS

| | | | |
|---|---|---|---|
| 4,223,679 | 9/1980 | Schulman et al. | 128/419 PT |
| 4,281,664 | 8/1981 | Duggan | 128/696 |
| 4,453,162 | 6/1984 | Money et al. | 340/19 |
| 4,494,545 | 1/1985 | Slocum et al. | 128/419 P |
| 4,556,063 | 12/1985 | Thompson et al. | 128/419 PT |
| 4,741,340 | 5/1988 | Batina et al. | 128/419 PT |

OTHER PUBLICATIONS

Coherent Demodulation of Frequency-Shift Keying With Low Duration Ratio, deBuda et al, IEEE Transactions on Communications, Jun. 1972, pp. 429-435.

Minimum-Shift-Keying Modum for Digitized-Voice Communications, Sass et al, RCA Journal, 1974.

Primary Examiner—Donald J. Yusko
Assistant Examiner—Tyrone Queen
Attorney, Agent, or Firm—Leslie S. Miller

[57] ABSTRACT

A telemetry system for use with implantable medical devices is disclosed which utilizes both in-phase and quadrature data components, and frequency modulates both data components into a single transmitted sinusoidal signal which varies in frequency between two selected frequencies. The signal is received and decoded, preferably by a coherent decoder, into in-phase and quadrature components, which are then integrated and sampled to produce the two transmitted in-phase and quadrature data components, which may then be recombined to produce the transmitted data. The system requires only low power, and is capable of operating at a relatively high data rate while retaining a high degree of accuracy due to the splitting of the signal into the in-phase and quadrature data components.

22 Claims, 4 Drawing Sheets

HIGH SPEED DIGITAL TELEMETRY SYSTEM FOR IMPLANTABLE DEVICES

BACKGROUND OF THE INVENTION

Field of the Invention

The present invention relates generally to a telemetry system for use in medical devices of various types and for various purposes implantable within the human body, and more particularly to a telemetry system which will transmit data at a relatively high rate in both directions while retaining a high degree of accuracy.

With the ever-shrinking size of electronic circuitry, the implantation into the human body of electronic medical devices has become more and more common. Although the most commonly known of such devices is the cardiac pacemaker, there are a variety of devices which are implanted into the human body, including devices for the stimulation or tenting, or both, of the brain, nerves, the spinal cord, muscles, bones, glands, or other body organs or tissues.

It will be appreciated by those skilled in the art that such implantable devices are becoming increasingly complex, and that more functions can be crammed into a relatively smaller electronic chip or circuit. Implantable medical devices have used bidirectional telemetry for a number of years. Information transmitted between the implanted device and an external transceiver may include, for example, device identification information, biological data, current operational parameters of the device, technical information regarding proper operation of the device, battery charge condition, revised operational parameters (programming information) for the device, and verification of information transmitted between the implanted device and the external transceiver.

With an ever-increasing amount of data being processed and available within the implantable device, there has been a corresponding increase in the need to transmit more data from the implanted device to the external transceiver for analysis, reprogramming of the implantable device, or other purposes. The need for more data to be transmitted in both directions has increased tremendously the amount of time required both to interrogate the implanted device and to reprogram the implanted device. An upper limit on the amount of data flowing between the implanted device and the external transceiver has therefore become directly proportional to the amount of time which may reasonably be taken to interrogate and reprogram the implanted device.

Accordingly, it is desirable to achieve a higher rate of data transfer between the implanted device and the external transceiver to eliminate this artificial impediment and to maximize the communication between the implanted device and the external transceiver. Of course, an increase in the rate of data exchange may not be obtained at the expense of accuracy in a medical device, particularly if the device is a life-sustaining device such as a pacemaker. Absolute accuracy is required, and it is apparent that an increase in the rate of data transfer will be nullified by an increase in the amount of time spent to verify data to ensure the degree of accuracy required.

The recent development of LSI circuits incorporating low current analog-to-digital converters has made the use of such converters in implantable devices possible. There are, of course, limitations surrounding the design of new implantable systems or portions thereof, the most limiting of which is the consumption of energy by the system. Implanted systems are customarily powered by a long-lasting non-replaceable internal battery, and the current consumption of a telemetry sub-system thus becomes perhaps the most important design factor to be considered.

Previously known devices have established various methods of communicating non-invasively through the skin. For example, U.S. Pat. No. 4,223,679, to Schulman et al., which patent is assigned to the assignee of the present invention, shows an implanted device which uses little or no current to transmit information by relying on reflected impedance of an internal L-C circuit. Internal modulation circuits in the implanted device transmit digital or analog data by modulating the reflected impedance, and the external transceiver utilizes an oscillator having varying frequency and amplitude outputs determined by a coupled RF magnetic field carrier to an L-C circuit in the external transceiver. This system works well, but, unfortunately, has speed limitations making it unsuitable for transmitting the amount of information contemplated herein.

Another type of device uses an active type transmitter, with the transmitted energy being taken from the implantable device battery. This type of device, which is illustrated in U.S. Pat. No. 4,281,664, to Duggan, has a data rate which is limited to approximately 100 BPS (bits per second). Another device which utilizes an active type transmitter is shown in U.S. Pat. No. 4,453,162, to Money et al. The Money et al. device can not achieve more than 0.25 to 0.05 bps/carrier cycle, a rate too low for the applications contemplated herein.

Those skilled in the art will also appreciate that it is not practical to increase the carrier frequency above approximately eight kHz, since the metal enclosure of the implanted device will experience eddy currents great enough to attenuate the signal significantly. In addition, increasing the carrier frequency makes electromagnetic interference from video display terminals, which are generally approximately 16 kHz, a significant problem. Consequently, techniques requiring a number of carrier cycles for each signal bit will be capable of achieving a speed only two to four kBPS.

It will therefore be appreciated that there exists a substantial need for a telemetry system which is capable of accurately transmitting and receiving data at a rate enabling the substantial amounts of data used by current implantable systems to be conveniently sent in a relatively short period of time. The amount of power required by the implanted portion of the system must be minimal, so as not to adversely affect battery life. Finally, the system should be compact so as to not add significantly to the space required by the implanted device.

SUMMARY OF THE INVENTION

The disadvantages and limitations of the background art discussed above are overcome by the present invention. With this invention, a circuit using an active transmitter can achieve a bit rate equal to or higher than the carrier frequency, thereby achieving a practical speed of about eight kBPS. Also, the circuit of the present invention uses a drive circuit which achieves high power efficiency.

In accordance with the present invention an inductor in the implantable device is used to generate a magnetic field through which information may be transmitted to an external receiver. The inductor is then tuned to one of two frequencies by using either one or two capacitors connected in parallel across the inductor. While transmitting data, one of the capacitors is permanently connected in parallel across the inductor, and determines the first resonant frequency of the system.

One side of the second capacitor is connected to one side of the parallel first capacitor and inductor combination; the other side of the second capacitor is connected to one side of a switch, the other side of which switch is connected to the other side of the parallel first capacitor and inductor combination. Whenever the switch is closed, the second capacitor will be connected in parallel together with the first capacitor and the inductor, and the resulting tuned circuit will resonate at a second frequency.

The external transceiver will contain means for decoding the first and second frequency carriers and for recovering the original data which was coded and transmitted. It will be understood that the process may be reversed to transmit data from the external transceiver to the implanted device.

In the preferred embodiment, the second frequency is selected to be equal to the first frequency minus half the signaling bit rate. The switch is controlled such that it is open when a "0" is to be transmitted, and closed when a "1" is to be transmitted, with the switch position being changed at the bit boundaries. The tuned circuit is energized for a short period of time each time its voltage reaches a positive or a negative peak by connecting it at the right polarity to the implanted device power source. The bit rate is chosen such that during a bit interval the tuned circuit voltage has an excursion of an integer number of peak-to-peak voltages.

By energizing the tuned circuit while its voltage passes through positive and negative peaks, as opposed to energizing it during only one polarity peak, sine wave distortion is reduced and the higher harmonic content, which is synonymous with lost energy, is reduced, thereby increasing transmitter power efficiency. In addition, as will become apparent from the following description, the method of switching between the first and second frequencies allows a constant amplitude carrier to be transmitted, as opposed to pulsing a carrier on and off, or abruptly changing the carrier phase.

The system of the present invention thereby achieves a reliable transmission at a higher signal to noise ratio, and at an implicitly lower average transmitter power, which features are very important for an implantable device. Also, by avoiding sharp amplitude and phase changes, the signal may be received by using only a relatively small bandwidth, which in turn both reduces the noise and permits operation of the transmitter at lower power. The maximum bit rate may therefore be equal to the first frequency. This was not possible in prior art systems, for in order to detect an amplitude modulated signal it requires more than one period (typically more than four periods) of the carrier.

Similarly, phase modulation as illustrated in Money et al. reference cited above will not achieve a bit rate equal to the first frequency. Thus, by energizing the tuned circuit during both positive and negative voltage excursions and by having the two tuning capacitors connected to the inductor, a maximum speed of approximately eight kBPS may be achieved. The system of the present invention is thereby capable of accurately transmitting and receiving data at a rate which enables the substantial amounts of data used by current implantable systems to be conveniently sent in a relatively short period of time. The amount of power required by the implanted portion of the system is minimal, thereby extending battery life. The system of the present invention is also quite compact, thereby fitting conveniently in the small space afforded by the implanted device. All of the above advantages are obtained without an relative disadvantage, making the system of the present invention a highly desirable improvement to the art.

DESCRIPTION OF THE DRAWINGS

These and other advantages of the present invention are best understood with reference to the drawings, in which.

DETAILED DESCRIPTION OF THE PREFERRED EMBODIMENT

Figure 1:
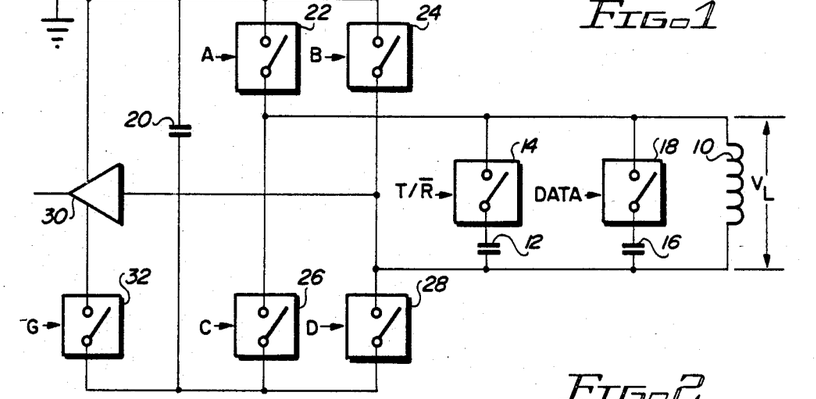
FIG. 1 is an electrical schematic of the implanted transceiver driver circuit of the present invention.

The preferred embodiment utilizes the circuit illustrated in FIG. 1 in the implanted device to transmit and receive information to and from an external device (not shown in FIG. 1). An inductor or coil 10 is tuned to a first frequency $f_1$ by a first capacitor 12 which is connected on one side thereof to one side of the inductor 10, and on the other side thereof to one side of a semiconductor switch 14. The other side of the semiconductor switch 14 is connected to the other side of the inductor 10, and it will be appreciated that when the switch 14 is closed, the first capacitor 12 will be connected in parallel with the inductor 10. The circuit will resonate at the first frequency $f_1$ in an essentially sinusoidal fashion, with a slowly decaying sinusoidal voltage $V_L$ across the inductor 10. The semiconductor switch 14 may be a transmission gate type device.

During transmission of data from the implanted device to the external device, the switch 14 is turned on or closed controlled by an input signal which is of high or true logic value, and which indicated that data is to be transmitted from the internal device to the external device. When data is to be received by the implanted device from the external device, the switch 14 will be turned off or opened.

The device may be tuned to a second frequency $f_2$ which is lower than the first frequency $f_1$ and which may be realized by installing a second capacitor 16 in parallel across the first capacitor 12 and the inductor 10. One side of the second capacator 16 is connected to the one side of the inductor 10, and the other side of the second capacitor 16 is connected to a second switch 18. The other side of the second switch 18 is connected to the other side of the inductor 10. The second switch 18 may be opened and closed to transmit binary data; in the embodiment discussed herein, for example, the second switch 18 will be turned on or closed when the data is to be serially transmitted is a logical "1", and turned off or opened when the data to be serially transmitted is a logical "0". When the second switch 18 is closed, the circuit will resonate at the second frequency $f_2$ in an essentially sinusoidal fashion, also with a slowly decaying sinusoidal voltage $V_L$ across the inductor 10. The semiconductor switch 18 may also be a transmission gate type device.

Four semiconductor switches are connected as a bridge circuit to a power source 20, which is typically the battery powering the implanted device. A first bridge switch 22 is connected on one side thereof to one side of the power source 20, and on the other side thereof to the other side of the inductor 10. A second bridge switch 24 is connected on one side thereof to the one side of the power source 20, and on the other side thereof to the one side of the inductor 10. A third bridge switch 26 is connected on one side thereof to the other side of the power source 20, and on the other side thereof to the other side of the inductor 10. Finally, a fourth bridge switch 28 is connected on one side thereof to other side of the power source 20, and on the other side thereof to the one side of the inductor 10.

It will be appreciated that the four bridge switches 22, 24, 26, and 28 are turned off or opened most of the time. The four bridge switches 22, 24, 26, and 28 are operated by control signals A, B, C, and D, respectively. For short periods of time approximately coinciding with positive peaks of coil voltage $V_L$ as oriented in FIG. 1, the first and fourth switches 22 and 28 are briefly closed. Similarly, when $V_L$ approximately reaches negative peaks, the second and third switches 24 and 26 are briefly closed. In this way, a permanent oscillation of the tuned circuit at virtually constant amplitude is maintained.

For example, the first and second switches 22 and 24 may be P-MOS transistors, and the third and fourth switches 26 and 28 may be N-MOS transistors. The first and second switches 22 and 24 are then open when their relative control signals A and B are a logical "1" and closed when their relative control signals are a logical "0". The third and fourth switches 26 and 28 are open when their relative control signals C and D are a logical "0" and closed when their relative control signals are a logical "1".

Figure 2:
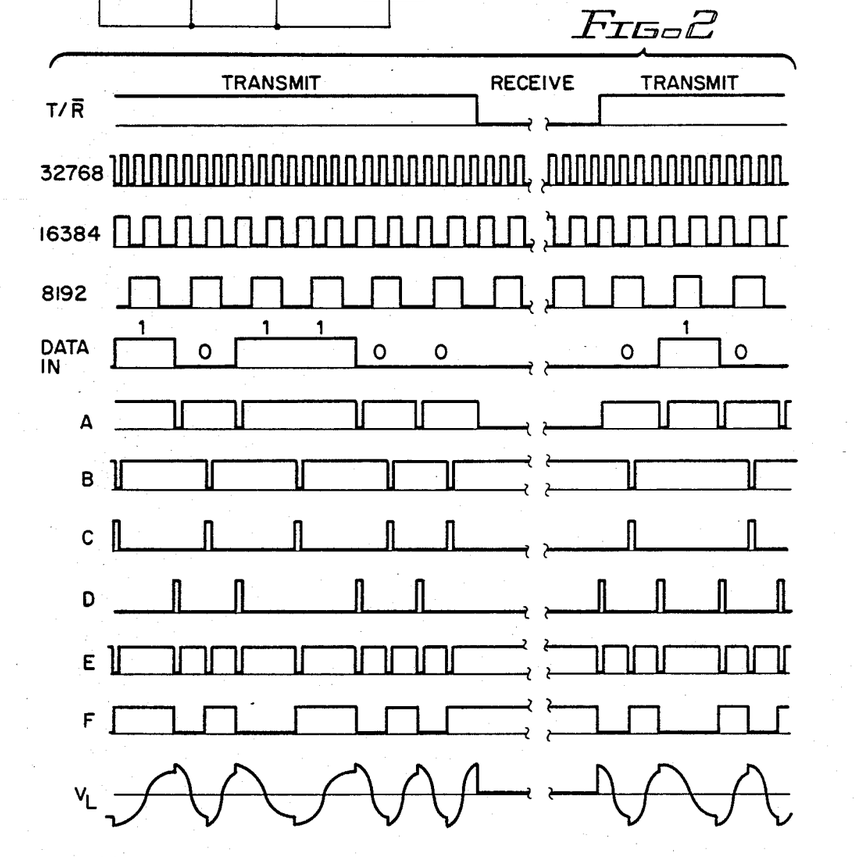
FIG. 2 is a timing diagram of control and output signals for the circuit shown in FIG. 1.

Referring now to FIG. 2 in conjunction with FIG. 1, it is apparent that the signal $V_L$ has a constant frequency, either the first frequency $f_1$ or the second frequency $f_2$, during each bit internal. In the preferred embodiment the first frequency $f_1$ is 8192 Hz and the second frequency $f_2$ is 4096 Hz. Their difference, 8192 Hz minus 4096 Hz, is 4096 Hz, which is half the bit rate of 8192 BPS.

In the preferred embodiment, the second frequency is selected to be equal to the first frequency minus half the signaling bit rate $f_R$, which is the reciprocal of the bit duration T. By selecting these frequencies, during each bit interval the voltage $V_L$ on the inductor 10 will start and stop on a peak value. The average current drawn from the power source 20 is very small, since during each supplying pulse the tuned circuit amplitude has to be increased only slightly to compensate for the natural decay in amplitude due to the limited quality factor (Q) of the coil.

The supply of electrical energy to the circuit in brief pulses during both positive and negative voltage peaks, as opposed to a supply in pulse mode during only either positive or negative peaks, has the advantage of reducing distortion of the fundamental 8192 Hz or 4096 Hz sine waves. Lower distortion of course yields higher power efficiency, since the distortion is comprised of harmonics which will be discarded by the receiver (not shown in FIGS. 1 or 2).

While a data "0" is transmitted by the implanted device, the second capacitor 16 is disconnected by the second switch 18. However, the charge (or voltage) is stored on the second capacitor 16, and is reused when the next data "1" is transmitted because the $V_L$ polarity at the beginning of a bit to the beginning of the next consecutive bit never changes if a data "0" is transmitted. This important characteristic of the driving circuit provides that the circuit does not draw additional energy due to the transition in transmission from data "0" to data "1" and from data "1" to data "0".

The implanted device can also receive information from an external device which inductively couples signal into the inductor 10. During receiving, the "DATA" input control to the second switch 18 is turned low, opening the second switch 18, and the T/$\overline{\text{R}}$ input control to the switch 14 is turned low, opening the switch 14 and closing the first bridge switch 22 (see FIG. 1, and also FIG. 3, signal A). This configuration couples the inductor 10 to an implanted receiver 30, whose output is a binary signal available to be used to decode the information received from the external device.

Figure 3:
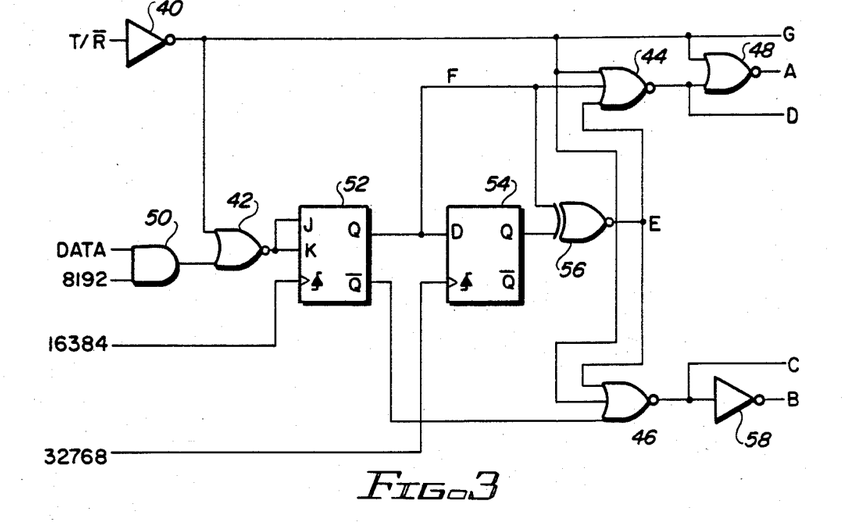
FIG. 3 is an electrical schematic of a circuit which may be used to generate the control signals shown in FIG. 2.

Optionally, a switch 32 will provide power to the receiver 30 only during periods when the receive function is being implemented. The control signal G, generated by the circuit of FIG. 3, is provided to control the switch 32. It should be noted that the T/$\overline{\text{R}}$ signal must be switched high and low only immediately before bit transition times. This ensures that no change on the first capacitor 12 or on the second capacitor 16 is lost, since after a receive period the transmit period will start with the same $V_L$ polarity as that left from the prior transmission period. Beyond this, the circuit of FIG. 3 does not require further explanation as it is common for those skilled in the art and may be implemented in a number of different ways.

FIG. 3 illustrates one possible example of a circuit which may be used to generate the control signals A, B, C, and D, and also to generate an additional control signal G. Inputs to the circuit of FIG. 3 are the transmit/receive line T/$\overline{\text{R}}$ which is also the input for the switch 14, the data line DATA which is also the input for the second switch 18, and three clock signals at 32768 Hz, 16384 Hz, and 8192 Hz. The source of the 32768 Hz signal may be derived from the crystal oscillator which is usually an integral part of implantable devices, as are the divided down frequencies of 16384 Hz, 8192 Hz, and 4096 Hz (used in FIG. 5). The control signal G is used to operate a receiver in the implanted device, and will be discussed below.

The transmit/receive line T/$\overline{\text{R}}$ is the input for a first inverter 40, the output of which is the control signal G. The control signal G is also supplied as an input to a first two input NOR gate 42, to a first three input NOR gate 44, to a second three input NOR gate 46, and to a second two input NOR gate 48. The DATA line and the 8192 Hz clock signal are the inputs for an AND gate 50, the output of which is an input for the first two input NOR gate 42. The output of the first two input NOR gate 42 is supplied as an input to both the J and K lines of a JK flip-flop 52, and the 16384 Hz clock signal is supplied to the JK flip-flop 52 as the clock signal.

The Q output of the JK flip-flop 52, which is shown in the timing charts of FIG. 2 as the control signal F, is supplied as an input to the D line of a D flip-flop 54, and as an input to a two input EXOR gate 56 and to the first three input NOR gate 44. The $\overline{Q}$ output of the JK flip-flop 52 is supplied as an input to the second three input NOR gate 46. The 32768 Hz clock signal is supplied as the clock signal to the D flip-flop 54, and the Q output of the D flip-flop 54 is supplied as an input to the two input EXOR gate 56.

The output of the two input EXOR gate 56, which is shown in the timing charts of FIG. 2 as the control signal E, is supplied as an input to the first three input NOR gate 44 and to the second three input NOR gate 46. The output of the first three input NOR gate 44 is the control signal D, and this output is supplied as an input to the second two input NOR gate 48. The output of the second two input NOR gate 48 is the control signal A. The output of the second three input NOR gate 46 is the control signal C, and this output is supplied as an input to a second inverter 58. The output of the second inverter 58 is the control signal B.

Figure 4:
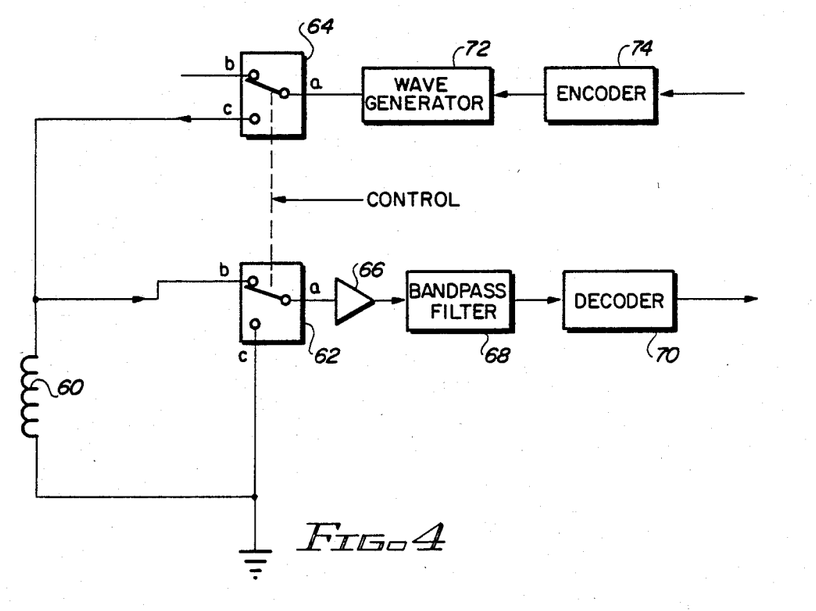
FIG. 4 is a functional schematic of the external transceiver for use with the implanted transceiver shown in FIG. 1.

The external transceiver used to receive data transmitted from the implanted device and to transmit data to the implanted device may now be discussed in conjunction with FIG. 4. A coil or inductor 60 is applied to the surface of the skin over the location of the inductor 10 of the implanted device. The two inductors 10 and 60 are constructed so that they will magnetically couple to each other. They may be regarded as two coils of a transformer having a low coupling coefficient.

A double pole, double throw switch is utilized in the external transceiver to switch between transmit and receive functions. Such a switch, which may be achieved either mechanically or electronically, is shown in FIG. 4 in schematic form as a first double pole switch 62 which is mechanically connected to and operating with a second double pole switch 64. Each of the double pole switches 62 and 64 has a switching contact a which is electrically connected to a contact b when the switches 62 and 64 are in a first position, and which is electrically connected to a contact c when the double pole switches 62 and 64 are in a second position.

The contact c of the first double pole switch 62 is connected to one side of the inductor 60. The contact b of the first double pole switch 62 and the contact c of the second double pole switch 64 are connected to the other side of the inductor 60. The contact b of the second double pole switch 64 is not used. The contact a of the first double pole switch 62 is connected to an input amplifier 66, the output of which is filtered by a bandpass filter 68 and then supplied to a decoder 70.

The contact c of the second double pole switch 64 is connected to the output of a wave generator 72, which has as its input information supplied from an encoder 74. Information to be transmitted from the external transceiver to the implanted device is supplied to the encoder 74, which encodes the information and supplied it to the wave generator 72. The wave generator 72 then supplies a waveform containing the encoded information. It will be appreciated by those skilled in the art that the wave generator 72 may function as does the circuit of FIG. 1 taught in this specification, or in other suitable ways known in the art. When the double pole switches 62 and 64 are in the second position, information may be transmitted from the external transceiver using the inductor 60, which will be connected to the wave generator 72 when the double pole switches 62 and 64 are in the second position.

When the double pole switches 62 and 64 are in the first position, the inductor 60 will be connected to the amplifier 66, and the external transceiver will act as a receiver. The voltage on the inductor 60 will be a replica of the signal $V_L$ on the inductor 10 of the implanted device (FIG. 1), but with a lower voltage amplitude due to the low coupling coefficient between the inductor 10 and the inductor 60. After this signal is amplified by the amplifier 66 and goes through the bandpass filter 68, it goes into the decoder 70, which looks at the signal morphology for the presence of the first or second frequencies $f_1$ or $f_2$, thereby deciding whether each bit interval of the transmission is a zero or a one.

Decoder circuits may be categorized as either coherent decoders or noncoherent decoders. Coherent decoders typically utilize phase locked loops or similar circuits to regenerate the two transmitted frequencies, and perform a correlation between these two frequencies and the received signal to decode the received signal. Noncoherent decoders are simpler, as they do not require a regeneration of the two transmitted frequencies. However, they require a higher signal-to-noise ratio in the received signal, which in turn requires higher implanted device transmitted power which is less desirable for use with a battery-powered implanted device. For the same transmitted power a coherent receiver will also provide a greater range, thereby allowing a larger distance between implanted and external inductor coils. A discussion of the coherent decoder is found in "Coherent Demodulation of Frequency shift Keying With Low Deviation Ratio," R. DeBuda, *IEEE Transactions on Communication*, June 1972.

Figure 5:
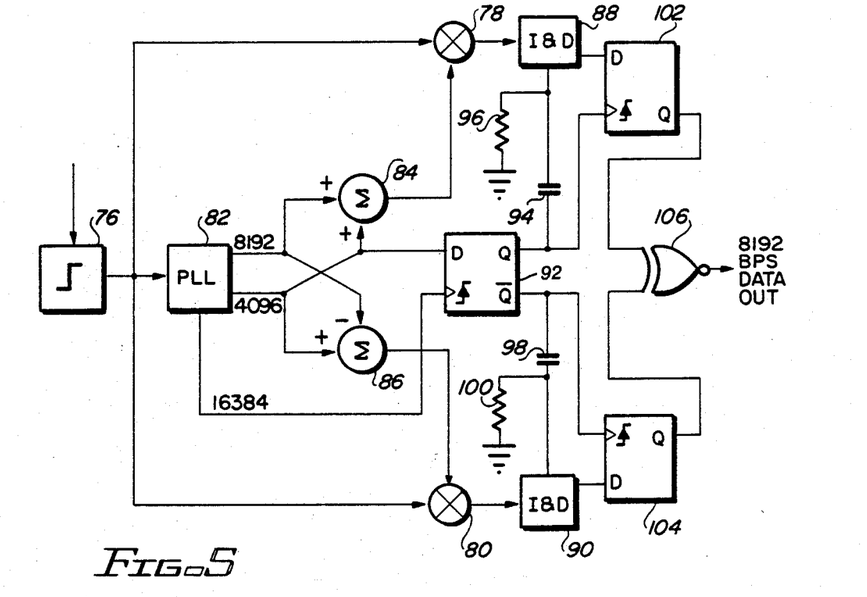
FIG. 5 is a functional schematic of a coherent decoder which may be used in the circuit of FIG. 4.
Figure 6:
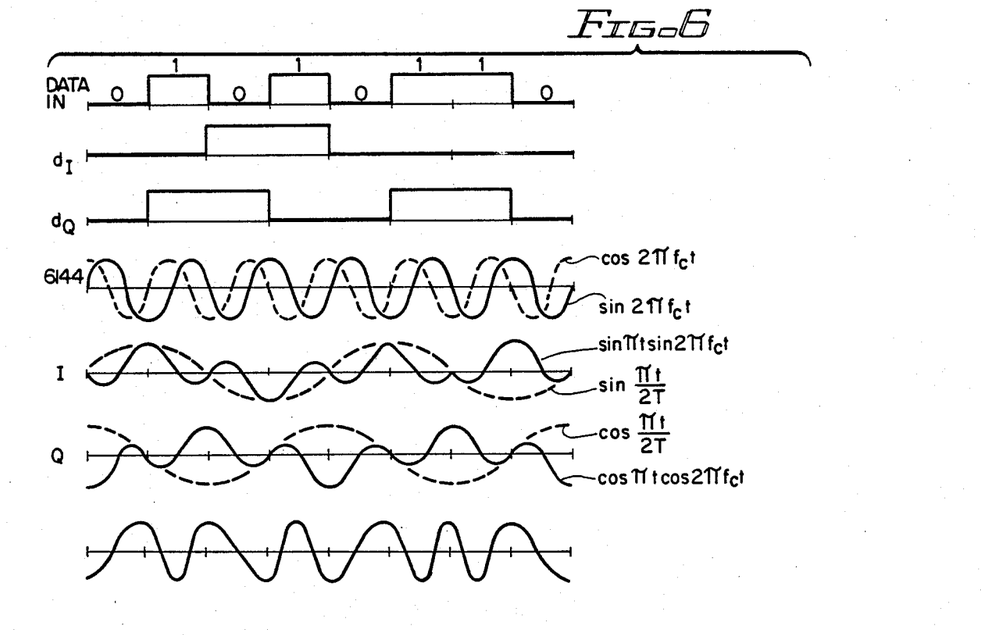
FIG. 6 is a diagram showing the data and output signals generated and transmitted by the implanted transceiver shown in FIG. 1.
Figure 7:
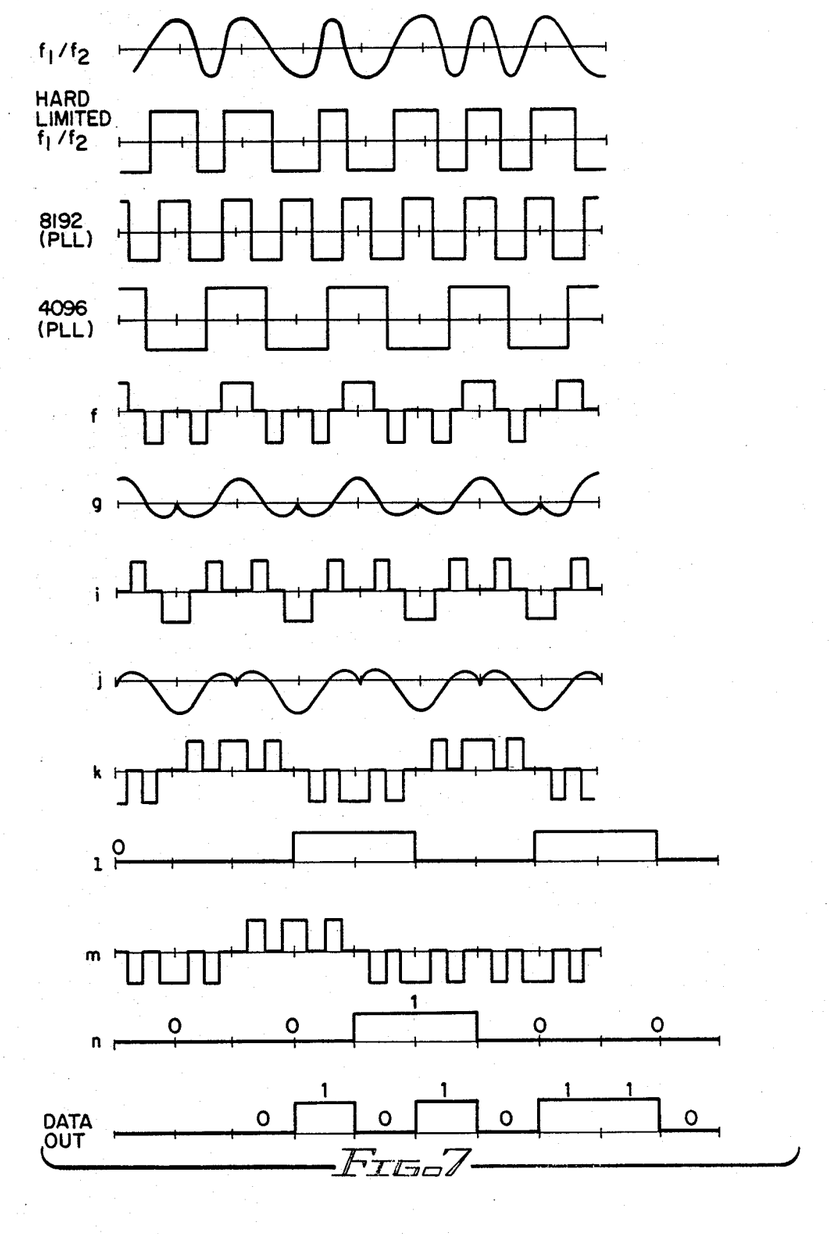
FIG. 7 is a diagram of signals generated by the coherent decoder of FIG. 5 which are used to decode the received signal of FIG. 6.

An example of a coherent decoder is shown in FIG. 5, which has as its input the amplified and filtered signal received from the implanted device. It is useful to discuss the operation of the coherent decoder in conjunction with an example of the transmission and receiving of data, and such an example is shown in FIGS. 6 and 7. In FIG. 6, a sample stream of data to be transmitted by the implanted device shown in FIG. 1 to the external transceiver shown in FIG. 4 is illustrated as DATA IN. This data may be thought of as the result of adding two streams of data, one with odd bits $d_I$ and the other with even bits $d_Q$.

The implanted device will transmit trains of two frequencies $f_1$ and $f_2$, as described above in conjunction with FIG. 1. The trains of frequencies $f_1$ and $f_2$ may be analytically viewed as a simultaneous transmission of two quadrature carriers (carriers having a 90 degree relative phase shift), with each binary phase being shift keyed or modulated by the data to be transmitted. The odd bits $d_I$ will modulate one carrier and the even bits $d_Q$ will modulate the other carrier.

As described above, in the preferred embodiment the second frequency $f_2$ is selected to be equal to the first frequency $f_1$ minus half the signaling bit rate $f_R$, which is the reciprocal of the bit duration T. The signaling bit rate $f_R$ of the preferred embodiment is 8192 BPS, the first frequency $f_1$ is 8192 Hz, and the second frequency $f_2$ is 4096 Hz, with the difference between $f_1$ and $f_2$ being 4096 Hz, which is half the signaling bit rate $f_R$ of 8192 BPS.

The frequency of the two carriers $f_1$ and $f_2$ can be trigonometrically demonstrated to be the arithmetic $f_1$ and $f_2$ average, which in this case is 6144 Hz. The advantage of this method lies in the fact that each bit now lasts 2T and the receiver has twice the time to make a decision whether the bit transmitted was a 0 or a 1, and as such is able to reject more noise. The transmitter need not be implemented as a two quadrature component system; only the receiver must be so constructed. FIG. 6 demonstrates how the two modulated 6144 Hz carriers I and Q are together equivalent to the $f_1/f_2$ train. The I (in-phase) and Q (quadrature) signals are also amplitude modulated with a maximum in the middle of each odd bit $d_I$ or even bit $d_Q$.

Referring again to FIG. 5, in conjunction with FIG. 7, the amplified and filtered $f_1/f_2$ signal received by the external transceiver is supplied to a hard limiter 76, the operation of which is known to those skilled in the art. Its output, the hard limited $f_1/f_2$ signal, has two binary states, positive or negative, according to polarity of the amplified and filtered $f_1/f_2$ signal. This hard limited $f_1/f_2$ signal is supplied to two multipliers, namely an I multiplier 78, and a Q multiplier 80. The function of the I multiplier 78 is to isolate the I (in-phase) component of the hard limited $f_1/f_2$ signal, and the function of the Q multiplier 80 is to isolate the Q (Quadrature) component of the hard limited $f_1/f_2$ signal.

The hard limited $f_1/f_2$ signal is also supplied to a phase-locked-loop circuit 82, where it is used to synchronize the clock signals provided as outputs from the phase-locked-loop circuit 82. The phase-locked-loop circuit 82 looks at the zero crossings of hard limited $f_1/f_2$ signal and adjusts the phase of its 4096 Hz, 8192 Hz, and 16384 Hz outputs to match the phase relationship of the received $f_1/f_2$ received by the external transceiver. The phase-locked-loop circuit 84 is not difficult to implement due to the special relations selected between the first frequency $f_1$, the second frequency $f_2$, and the signaling bit rate $f_R$ which is the reciprocal of the bit duration T, namely that the second frequency $f_2$ is one-half the first frequency $f_1$, and that the first frequency $f_1$ equal to the bit signaling rate $f_R$. The f and i signals have to be generated by the receiver.

Two modulated recovered carriers are generated by adding and subtracting the 8192 Hz and the 4096 Hz outputs from the phase-locked-loop circuit 82 together. A first summer 84 adds the 8192 Hz and the 4096 Hz outputs from the phase-locked-loop circuit 82 together to produce the modulated recovered I carrier f, which is shown in FIG. 7 together with the sinusoidal I carrier labeled as g for comparison. Similarly, a second summer 86 subtracts the 8192 Hz output of the phase-locked-loop circuit 82 from the 4096 Hz output of the phase-locked-loop circuit 82 to produce the modulated recovered Q carrier i, which is shown in FIG. 7 together with the sinusoidal Q carrier labeled as j for comparison.

It should be noted that the signals f and i are approximations to the exact sinusoidal signals g and j, respectively. However, any performance degradation resulting from this approximation is negligible, and does not require further complicating the circuit of FIG. 5 with filters to smooth the f and i signals into closer approximations of the g and j signals, respectively.

The I multiplier 78 multiplies the hard-limited $f_1/f_2$ signal by the modulated recovered I carrier f to isolate the I (in-phase) component of the hard limited $f_1/f_2$ signal. When the hard-limited $f_1/f_2$ signal is multiplied by the modulated recovered I carrier f in the I multiplier 78, the sign of the modulated recovered I carrier f is either changed if the hard-limited $f_1/f_2$ signal is negative or unchanged if the hard-limited $f_1/f_2$ signal is positive. The resulting signal which is supplied as the output of the I multiplier 78 is the signal k, shown in FIG. 7, which signal k is supplied to an integrate-and-dump device 88.

Similarly, the Q multiplier 80 multiplies the hard-limited $f_1/f_2$ signal by the modulated recovered Q carrier i to isolate the Q (quadrature) component of the hard limited $f_1/f_2$ signal. When the hard-limited $f_1/f_2$ signal is multiplied by the modulated recovered Q carrier i in the Q multiplier 80, the sign of the modulated recovered Q carrier i is either changed if the hard-limited $f_1/f_2$ signal is negative or unchanged if the hard-limited $f_1/f_2$ signal is positive. The resulting signal which is supplied as the output of the Q multiplier 80 is the signal m, shown in FIG. 7, which signal m is supplied to an integrate-and-dump device 90.

The 4096 Hz clock output of the phase-locked-loop circuit 82 is supplied as an input to the D line on a D flip-flop 92. The 16384 Hz clock output of the phase-locked-loop circuit 82 is supplied as the clock input to the D flip-flop 92 to regenerate the data bit clock thereof. The Q and $\overline{Q}$ outputs of the D flip-flop 92 are therefore a series of alternating 1's and 0's, with the period in which one 1 and one 0 occurs being 2T. The D flip-flop 92 may be seen as a sort of steering circuit, which alternately causes signals from the in-phase side and the quadrature side of the circuit of FIG. 5 to be combined to produce a single consolidated output.

The Q output of the D flip-flop 92 is connected to one side of a capacitor 94, the other side of which is connected to the integrate-and-dump device 88. A resistor 96 is connected on one side to ground, and on the other side to the other side of the capacitor 94. The capacitor 94 and the resistor 96 provide to the integrate-and-dump device 88 a series of pulses which occur shortly after the rising edges of the Q output of the D flip-flop 92. The integrate-and dump device 88 integrates the k signal, and at the occurrence of each pulse occurring after a rising edge of the Q output of the D flip-flop 92, the integrate-and-dump device 88 is reset.

The $\overline{Q}$ output of the D flip-flop 92 is connected to one side of a capacitor 98, the other side of which is connected to the integrate-and-dump device 90. A resistor 100 is connected on one side to ground, and on the other side to the other side of the capacitor 98. The capacitor 98 and the resistor 100 provide to the integrate-and-dump device 90 a series of pulses which occur shortly after the rising edges of the $\overline{Q}$ output of the D flip-flop 92. The integrate-and-dump device 90 integrates the m signal, and at the occurrence of each pulse occurring after a rising edge of the $\overline{Q}$ output of the D flip-flop 92, the integrate-and-dump device 90 is reset.

The integrate-and-dump devices 88 and 90 will produce an output reflecting the inputs thereto. If for the majority of the 2T period the input to one of the integrate-and-dump devices 88 and 90 is high, the output from that device at the end of the 2T period will be high. Similarly, if for the majority of the 2T period the input to one of the integrate-and-dump devices 88 and 90 is low, the output from that device at the end of the 2T period will be low. The integrate-and-dump devices 88 and 90 may thus be viewed as low-pass filters.

The output from the integrate-and-dump device 88 is supplied as an input to the D line on a D flip-flop 102, which has as its clock input the Q output from the D flip-flop 92. The output from the integrate-and-dump device 88 is therefore sampled by the D flip-flop 102 after each period of time of 2T and at the rising edge of the Q output of the D flip-flop 92, which period is that determined by the D flip-flop 92. The Q output from the D flip-flop 102 is the signal 1 shown in FIG. 7.

Likewise, the output from the integrate-and-dump device 90 is supplied as an input to the D line on a D flip-flop 104, which has as its clock input the $\overline{Q}$ output from the D flip-flop 92. The output from the integrate-and-dump device 90 is therefore sampled by the D flip-flop 104 after each period of time of 2T and at the rising edge of the $\overline{Q}$ output of the D flip-flop 92, which period is that determined by the D flip-flop 92. The Q output from the D flip-flop 104 is the signal n shown in FIG. 7.

It will be appreciated that the integrate and dump cycles of the integrate-and-dump device 88 and the integrate-and-dump device 90 and the flip-flop samples of the D flip-flop 102 and the D flip-flop 104 are alternating, and must be interleaved to produce a single output from the external transceiver reflecting the input from the implanted device. Accordingly, the Q output 1 from the D flip-flop 102 and the Q output n from the D flip-flop 104 are supplied as inputs to a two input EXOR gate 106, the output of which is the desired received data. It will be appreciated that the data output from the two input EXOR gate 106 shown in FIG. 7 will be time delayed by a period of 2T from the data input shown in FIG. 6. This delay is caused by the sampling of the integrate-and-dump devices 88 and 90 by the D flip-flops 102 and 104, respectively, once every period of 2T.

Alternatively to the coherent decoder of FIG. 5, a noncoherent decoder could be used to decode the $f_1/f_2$ signal. Noncoherent decoders, which are essentially envelope detectors, are well known in the art, but they would not work as well as coherent decoders at the relatively data frequency used herein. Because a coherent decoder has two parallel paths, and each path has a two bit interval (2T) to integrate the signal, a coherent decoder will necessarily have a better performance than the noncoherent decoder, and will be significantly more resistant to noise.

It will be appreciated by those skilled in the art that the system of the present invention achieves a reliable high rate of data transmission at a high signal to noise ratio, while requiring only low transmitter power, features which are very important for an implantable device. The signal is received using only a relatively small bandwidth, thereby both reducing noise and permitting operation of the transmitter at lower power. The maximum bit rate may be equal to the first frequency, a feature not possible in prior art systems, since in such systems in order to detect an amplitude modulated signal it required more than one period (typically more than four periods) of the carrier.

Also, by energizing the tuned circuit during both positive and negative voltage excursions and by having the two tuning capacitors connected to the inductor, a maximum speed of approximately eight kBPS may be achieved. The system of the present invention is capable of accurately transmitting and receiving data at a rate which enables the substantial amounts of data used by current implantable systems to be conveniently sent in a relatively short period of time. The amount of power required by the implanted portion of the system is minimal, thereby extending battery life, and the system of the present invention is quite compact. While attaining these advantages and features, no relative disadvantage is incurred.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A telemetry system for use with an implantable device, comprising:
    a DC power source;
    an inductor for generating an information-containing magnetic field;
    a first capacitor for connection in parallel across said inductor, said first capacitor when connected across said inductor tuning said inductor to a first frequency;
    a first switch for selectively connecting said first capacitor in parallel across said inductor when said first switch is closed and disconnecting said first capacitor from parallel connection across said inductor when said first switch is open, said first switch being closed when data is to be transmitted by said inductor;
    a second capacitor for connection in parallel across said inductor, said second capacitor when connected across said inductor with said first capacitor also connected across said inductor tuning said inductor to a second frequency;
    a second switch for selectively connecting said second capacitor in parallel across said inductor when said second switch is closed and disconnecting said second capacitor from parallel connection across said inductor when said second switch is open, said second switch being open both when no data is to be transmitted by said inductor and when a first digital binary signal is to be transmitted by said inductor, said second switch being closed when a second digital binary signal different from said first digital binary signal is to be transmitted by said inductor, said second switch being opened or closed only when the voltage across said inductor is approximately at either a positive or negative peak value; and
    means for periodically, briefly switching said power source into connection across each of said first and second capacitors to charge said first and second capacitors.

2. A telemetry system as defined in claim 1, wherein said DC power source is a battery used to provide power for the implantable device.

3. A telemetry system as defined in claim 1, wherein the second frequency is equal to the first frequency minus one-half the data bit rate, the data bit rate being the reciprocal of the bit duration T.

4. A telemetry system as defined in claim 3, wherein the bit duration T is selected to allow the voltage across the inductor to have an excursion of an integer number of peak-to-peak voltages.

5. A telemetry system as defined in claim 4, wherein the data bit rate is 8192 bits per second, the first frequency is 8192 bits per second, and the second frequency is 4096 bits per second.

6. A telemetry system as defined in claim 1, wherein a digital "0" is transmitted by said inductor when said first switch is closed and said second switch is open, and a digital "1" is transmitted by said inductor when both said first and said second switches are closed.

7. A telemetry system as defined in claim 1, wherein, said switching means only connects said power source to charge said first and second capacitors when said voltage across said inductor is approximately at positive and negative peak values.

8. A telemetry system as defined in claim 1, wherein said DC power source has a first terminal and a second terminal, said inductor has a first terminal and a second terminal, and said switching means comprises:
a first power switch having a first terminal and a second terminal, said first terminal of said first power switch being connected to said first terminal of said DC power source, said second terminal of said first power switch being connected to said first terminal of said inductor;
a second power switch having a first terminal and a second terminal, said first terminal of said second power switch being connected to said first terminal of said DC power source, said second terminal of said second power switch being connected to said second terminal of said inductor;
as third power switch having a first terminal and a second terminal, said first terminal of said third power switch being connected to said second terminal of said DC power source, said second terminal of said third power switch being connected to said first terminal of said inductor; and
a fourth power switch having a first terminal and a second terminal, said first terminal of said fourth power switch being connected to said second terminal of said DC power source, said second terminal of said fourth power switch being connected to said second terminal of said inductor.

9. A telemetry system as defined in claim 8, additionally comprising:
logic means for briefly closing said first and fourth power switches when said voltage across said inductor is approximately at a positive peak value, said logic means also for briefly closing said second and fourth power switches when said voltage across said inductor is approximately at a negative peak value.

10. A telemetry system as defined in claim 9, wherein said logic means operates to selectively close said first, second, third, and fourth power switches only when data is being transmitted.

11. A telemetry system as defined in claim 8, wherein said inductor is also used to receive an information-containing magnetic field, said telemetry system additionally comprising:
a receiver for use when data is being received by said inductor, said receiver being connected to and having as inputs said first terminal of said first power switch and said second terminal of said inductor, said first power switch being in a closed position when data is being received by said inductor.

12. A telemetry system as defined in claim 11, additionally comprising:
a fifth power switch having a first terminal and a second terminal, said first terminal of said fifth power switch being connected to said second terminal of said DC power source, said second terminal of said fifth power switch being connected to power said receiver.

13. A telemetry system as defined in claim 1, wherein said DC power source, said inductor, said first and second capacitors, said first and second switches, and said switching means are contained in said implantable device.

14. A telemetry system as defined in claim 13, wherein said inductor is also used to receive an information-containing magnetic field, said telemetry system additionally comprising an external device for receiving data transmitted from said implantable device and sending data to said implantable device, said external device comprising:
an external inductor for either generating an information-containing magnetic field or receiving an information-containing magnetic field;
means for supplying information to be transmitted to said implanted device;
means for receiving information from said implanted device; and
external switching means for selectively, alternately connecting said supplying means and said receiving means to said external inductor.

15. A telemetry system as defined in claim 14, wherein said supplying means comprises:
an encoder for encoding information to be transmitted to said implanted device; and
a wave generator for generating a waveform containing said encoded information.

16. A telemetry system as defined in claim 14, wherein said receiving means comprises:
means for amplifying data received from said implanted device;
bandpass filter means for filtering the amplified data from said amplifying means to remove noise; and
means for decoding the filtered, amplified data from said filter means into a digital data output signal.

17. A telemetry system as defined in claim 16, wherein said decoding means comprises:
a coherent decoder.

18. A telemetry system as defined in claim 16, wherein said decoding means comprises:
a noncoherent decoder.

19. A telemetry system for use with an implantable device and an external device, comprising:
a DC power source in said implantable device;
an inductor in said implantable device for generating an information-containing magnetic field;
a first capacitor in said implantable device for connection in parallel across said inductor, said first capacitor when connected across said inductor tuning said inductor to a first frequency;
a first switch in said implantable device for selectively connecting said first capacitor in parallel across said inductor when said first switch is closed and disconnecting said first capacitor from parallel connection across said inductor when said first switch is open, said first switch being closed when data is to be transmitted by said inductor;
a second capacitor in said implantable device for connection in parallel across said inductor, said second capacitor when connected across said inductor with said first capacitor also connected across said inductor tuning said inductor to a second frequency;
a second switch in said implantable device for selectively connecting said second capacitor in parallel across said inductor when said second switch is closed and disconnecting said second capacitor from parallel connection across said inductor when said second switch is open, said second switch being open both when no data is to be transmitted by said inductor and when a first digital binary signal is to be transmitted by said inductor, said second switch being closed when a second digital binary signal different from said first digital binary signal is to be transmitted by said inductor, said second switch being opened or closed only when the voltage across said inductor is approximatley at either a positive or negative peak value;

means in said implantable device for periodically, briefly switching said power source into connection across each of said first and second capacitors to charge said first and second capacitors when said voltage across said inductor is approximately at positive and negative peak values;

an external inductor in said external device for either generating an information-containing magnetic field or receiving an information-containing magnetic field a receiver located in said external device for receiving information received by said external inductor.

20. A telemetry system as defined in claim 19, wherein said inductor is also used to receive an information-containing magnetic field, said telemetry system additionally comprising:

a receiver for use when data is being received by said inductor, said receiver being connected to said inductor by said switching means when data is being received by said inductor;

a transmitter located in said external device for supplying information to be transmitted by said external inductor; and external means located in said external device for selectively, alternately connecting said external inductor to said receiver and said transmitter.

21. A method of telemetering data from an implantable device to an external device, comprising:

generating an information-containing magnetic field with an inductor;

selectively tuning said information-containing magnetic field to a first frequency or to a second frequency, said information-containing magnetic field being tuned to said first frequency by connecting a first capacitor across said inductor when a first digital binary signal is to be transmitted by said information-containing magnetic field, said information-containing magnetic field being tuned to said second frequency by connecting both said first capacitor and a second capacitor across said inductor when a second digital binary signal different from said first digital binary signal is to be transmitted by said information-containing magnetic field;

periodically, briefly energizing each of said first and second capacitors to charge said first and second capacitors, respectively, when the voltage across said inductor is approximately either a positive or negative peak; and receiving said information-containing magnetic field and deriving the information contained therein therefrom.

22. A telemetry system as defined in claim 1, wherein a digital "1" is transmitted by said inductor when said first switch is closed and said second switch is open, and a digital "0" is transmitted by said inductor when both said first and said second switches are closed.

* * * * *